(12) United States Patent
Tchao et al.

(10) Patent No.: US 10,441,718 B2
(45) Date of Patent: Oct. 15, 2019

(54) DEVICE FOR THE PREVENTION OF OVERDOSE BY OPIATE AND DEPRESSANT USERS

(71) Applicant: David Tchao, Dix Hills, NY (US)

(72) Inventors: David Tchao, Dix Hills, NY (US); Paul Tchao, Dix Hills, NY (US)

( * ) Notice: Subject to any disclaimer, the term of this patent is extended or adjusted under 35 U.S.C. 154(b) by 344 days.

(21) Appl. No.: 15/054,111

(22) Filed: Feb. 25, 2016

(65) Prior Publication Data
US 2017/0246390 A1    Aug. 31, 2017

(51) Int. Cl.

| | | |
|---|---|---|
| *A61M 5/172* | (2006.01) | |
| *A61K 31/137* | (2006.01) | |
| *A61M 15/08* | (2006.01) | |
| *A61K 38/26* | (2006.01) | |
| *A61K 31/56* | (2006.01) | |
| *A61K 31/167* | (2006.01) | |
| *A61K 31/46* | (2006.01) | |
| *A61B 5/00* | (2006.01) | |
| *A61B 5/0205* | (2006.01) | |
| *A61B 5/1455* | (2006.01) | |
| *A61B 5/145* | (2006.01) | |
| *A61B 5/0452* | (2006.01) | |
| *A61K 38/28* | (2006.01) | |
| *A61M 5/142* | (2006.01) | |
| *A61B 5/021* | (2006.01) | |
| *A61B 5/024* | (2006.01) | |
| *A61M 5/20* | (2006.01) | |

(52) U.S. Cl.
CPC ......... *A61M 5/1723* (2013.01); *A61B 5/0205* (2013.01); *A61B 5/0452* (2013.01); *A61B 5/14532* (2013.01); *A61B 5/14551* (2013.01); *A61B 5/4839* (2013.01); *A61B 5/746* (2013.01); *A61K 31/137* (2013.01); *A61K 31/167* (2013.01); *A61K 31/46* (2013.01); *A61K 31/56* (2013.01); *A61K 38/26* (2013.01); *A61K 38/28* (2013.01); *A61M 5/14244* (2013.01); *A61M 15/085* (2014.02); *A61B 5/021* (2013.01); *A61B 5/02438* (2013.01); *A61B 5/4845* (2013.01); *A61B 5/6819* (2013.01); *A61B 5/6824* (2013.01); *A61M 5/2053* (2013.01); *A61M 2202/049* (2013.01); *A61M 2205/3592* (2013.01); *A61M 2205/50* (2013.01); *A61M 2205/8206* (2013.01); *A61M 2205/8225* (2013.01); *A61M 2230/06* (2013.01); *A61M 2230/30* (2013.01)

(58) Field of Classification Search
CPC . A61M 5/1723; A61M 15/085; A61B 5/0205; A61B 5/0452
USPC .......................................................... 604/66
See application file for complete search history.

(56) References Cited

U.S. PATENT DOCUMENTS

| | | | | |
|---|---|---|---|---|
| 2008/0294096 | A1* | 11/2008 | Uber, III | ............... A61M 5/142 604/66 |
| 2011/0137290 | A1* | 6/2011 | Flickinger | .............. A61M 11/06 604/514 |

\* cited by examiner

*Primary Examiner* — Phillip A Gray

(57) ABSTRACT

An automated wearable device measure physiological signals, and when parameters which cause the wearer to be at risk are measured, the device delivers an antidote for a given medical condition. This prevents overdose or medical conditions from occurring.

14 Claims, 5 Drawing Sheets

DEVICE FOR THE PREVENTION OF OVERDOSE BY OPIATE AND DEPRESSANT USERS

FIELD OF THE INVENTION

The field of the invention is medical devices.

BACKGROUND OF THE INVENTION

Opiate addiction is the leading cause of death among adults under twenty-four in many regions of the United States. Opiates are powerfully addictive since they bind with greater affinity than the body's natural dopamine. The majority of opiate users today start their addiction with prescription drugs. When they can no longer afford prescription opiates, they often turn to heroin use. According to the Center for Disease Control, 44 Americans die every day in the US from opiates.

Drug overdose is caused by a variety of effects on the body. Opiates slow down breathing, heart rate, and drop blood pressure to fatal levels. The opiate user is impaired and incapable of self-administering antidote such as adrenaline or naloxone. In addition, medical professionals such as physicians and emergency-medical-technicians are often unaware of the causes of the loss of consciousness and may accidentally mis-prescribe the intervention procedure.

Much of the prior art is driven by the desire to deal with chronic conditions, such as diabetes, or constant medication for a given conditioning, in order to reduce the labor associated with repeated regular treatment.

Syringe-based injection systems exist in a variety of applications in the public domain. Bryant Jr et al. in U.S. Pat. No. 9,132,227 describe an infusion pump for the introduction of liquids intravenously. U.S. Pat. No. 9,114,208 describes a medication delivery device with a cartridge system. In U.S. Pat. No. 9,101,707 an implantable delivery system for bio-secretions is disclosed.

The inventors in U.S. Pat. No. 9,095,650 have a precision piston syringe system. In U.S. Pat. No. 9,067,047 a programmable injection system is described by the inventors. These are all developments which seek to attain automation or continuous drug delivery. In U.S. Pat. No. 9,061,097 Holt et al. U.S. Pat. No. 9,061,097 a wearable drug delivery system is described. It has a disposable cartridge system for single dosage use. Chong et al. U.S. Pat. No. 8,979,808 describe an on-body injection device. Sonderger et al. describe a device with a rechargeable syringe delivery system. In another invention in the prior art, Trembly III et al, U.S. Pat. No. 8,747,358 describe an injection system with manual control instead of automation. This allows control by the patient or care giver, especially when the prior is disabled or unable to use a loose syringe.

OBJECTS OF THE INVENTION

One object of the invention is to develop an automated injection system which uses vital signs to be activated. Yet another object of the invention is to develop a wearable drug delivery system. Yet another object of the invention is to develop a device for opiate overdose prevention. Another object of the invention is to develop a device which radio signals medical professionals with information from an overdosing patient. Yet another object of the invention is to block opiate overdose by means of nasal spray vectored antidote.

SUMMARY OF THE INVENTION

The invention is a wearable band containing an electronic vital-signs detector linked to an electronic activated drug syrette. When the wearer's blood pressure and pulse drop off indicating an overdose, the syrette with antidote is activated and administered automatically.

DETAILED DESCRIPTION OF THE INVENTION

A wearable band 10 (FIG. 1) contains electrodes or other sensors 7 to detect pulse and blood pressure levels. This data is sent to a small central processing unit 9 contained inside the band 10. The device contains an injectable syrette 5 with medication which is automatically injected when the device registers abnormally low pulse or blood pressure. When this occurs, a radio signal is emitted which allows for the wearer to both be located, and pre-diagnosed by medical personnel en route to the location. The radio signal contains the location of the wearer, the blood pressure, and pulse, as well as an announcement that the condition is drug induced.

EXAMPLES

Figure 1:
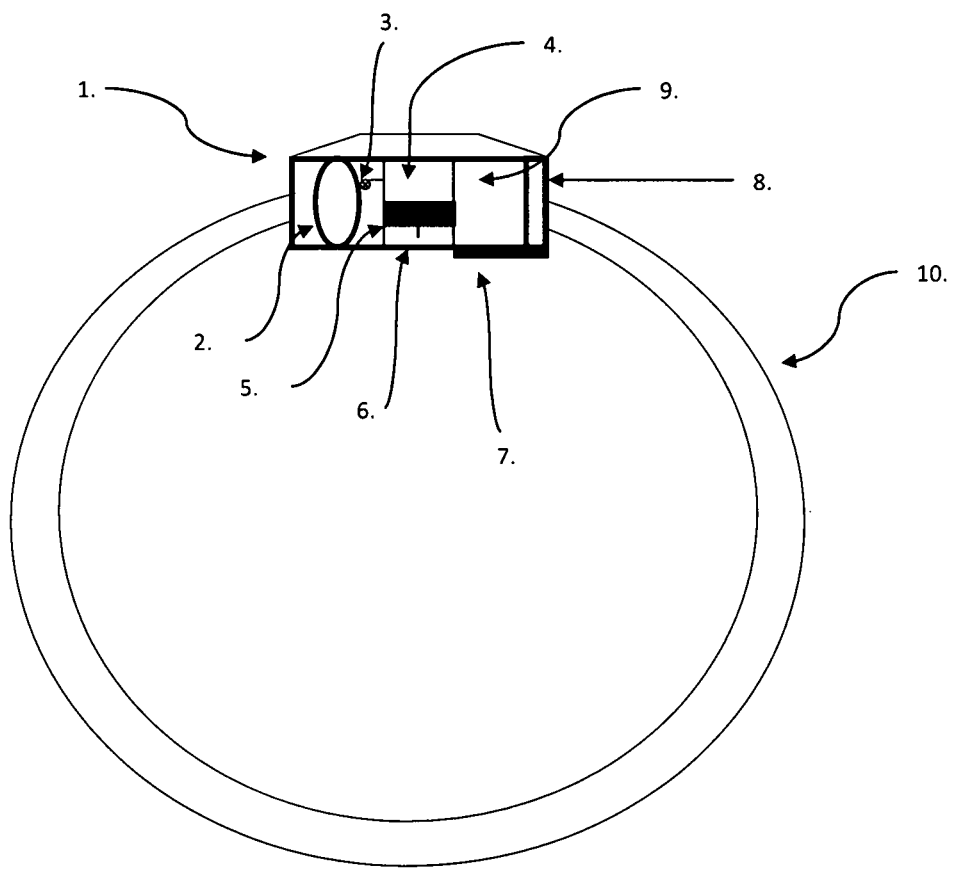
FIG. 1 illustrates a wearable band having a compressed gas cylinder for injecting an antidote.

In a preferred embodiment of the invention, illustrated in FIG. 1, the unit is a rectangular flat device with lateral attached rods which serve as band attachment points. The device is 2 inches squared in surface area and one inch to one-half inches thick on its profile. The rectangular device housing 1 contains a small central processing unit 9 which has wire relays to a radioemitter, a gas-release valve 3, and two blood pressure and pulse sensors 7. When the blood-pressure and pulse sensors 7 measure values and frequency which indicate that the wearer is undergoing an overdose, the central processing unit 9 simultaneously opens a gas release valve 3 which sends a pressurized gas powered syrette 5 into the limb of the wearer, emptying the syrette's 5 contents into the bloodstream, while simultaneously sending out an emergency radio signal indicating where the wearer is, and what the physiological data is, and that the wearer is a drug user, to prepare the medical intervention.

The syrette 5 is in the configuration of a thumb tac. The reservoir is flush with the edges of the cylinder 2, which when filled with compressed gas, acts as a gas-piston to drive the syrette 5 down through a permeable membrane 6, and further compresses the compressible syrette 5 to inject the medication. Preferred embodiments include the use of noxalone and adrenaline as opiate antidotes. The central processing unit 9 has a built-in battery 8 or uses a small hearing aid battery to power normal function and emergency activation. A small pressurized replaceable gas cylinder 2 fits into a chamber which is connected by the syrette piston chamber 4 by a small gas channel controlled by an electrically activated gas-release valve 3. The central processing unit 9 only activates the valve release as well as the radio emitter in critical physiological function declines past acceptable levels. Once this occurs, pressurized gas is released from the compressed gas cylinder 2 via a gas release valve 3 controlled by the central processing unit 9. This gas plunges the syrette 5 into the wearer. and further gas compression collapses the reservoir injecting the drug. The radio emitter simultaneously emits a signal.

Figure 2:
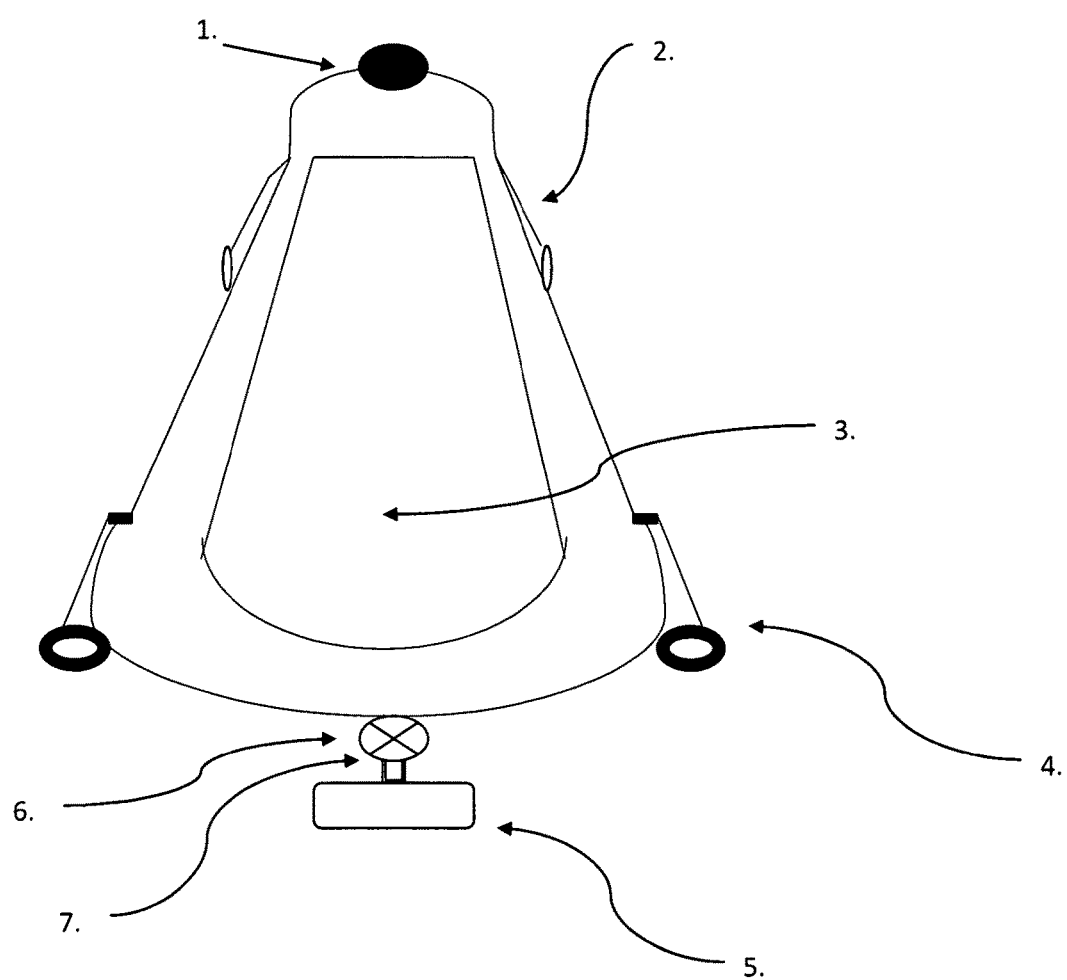
FIG. 2 illustrates a wearable gas mask for delivering an antidote into a wearer's face for inhalation.

In another preferred embodiment, as illustrated by FIG. 2/5, the device is in the form of a wearable gas mask configuration which has a seal around the wearers face and a transparent material 3 which allows the wearer to see and be seen. A central-processing-unit 2 and radio and actuator simultaneously measures physiological signals, emits a radio alarm, and releases the compressed antidote 5 as a mist into the facemask where it is inhaled to be absorbed through the sinuses and lungs.

Figure 3:
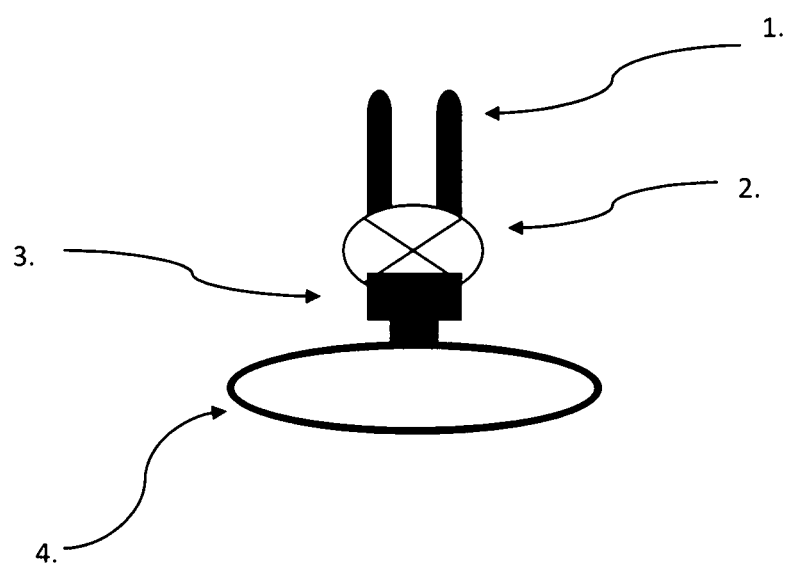
FIG. 3 shows a nose clip device for delivering an antidote via a compressed gas cylinder into the nostrils.

In another preferred embodiment, as illustrated in FIG. 3. the opiate antidote medicine is supplied as a nasal mist via a nose-clip 1. In this preferred embodiment, the device is activated when it senses decreased breathing and pulse. It actively sprays the antidote into the sinuses via a compressed gas cylinder 4 propelling the antidote into the sinuses.

Figure 4:
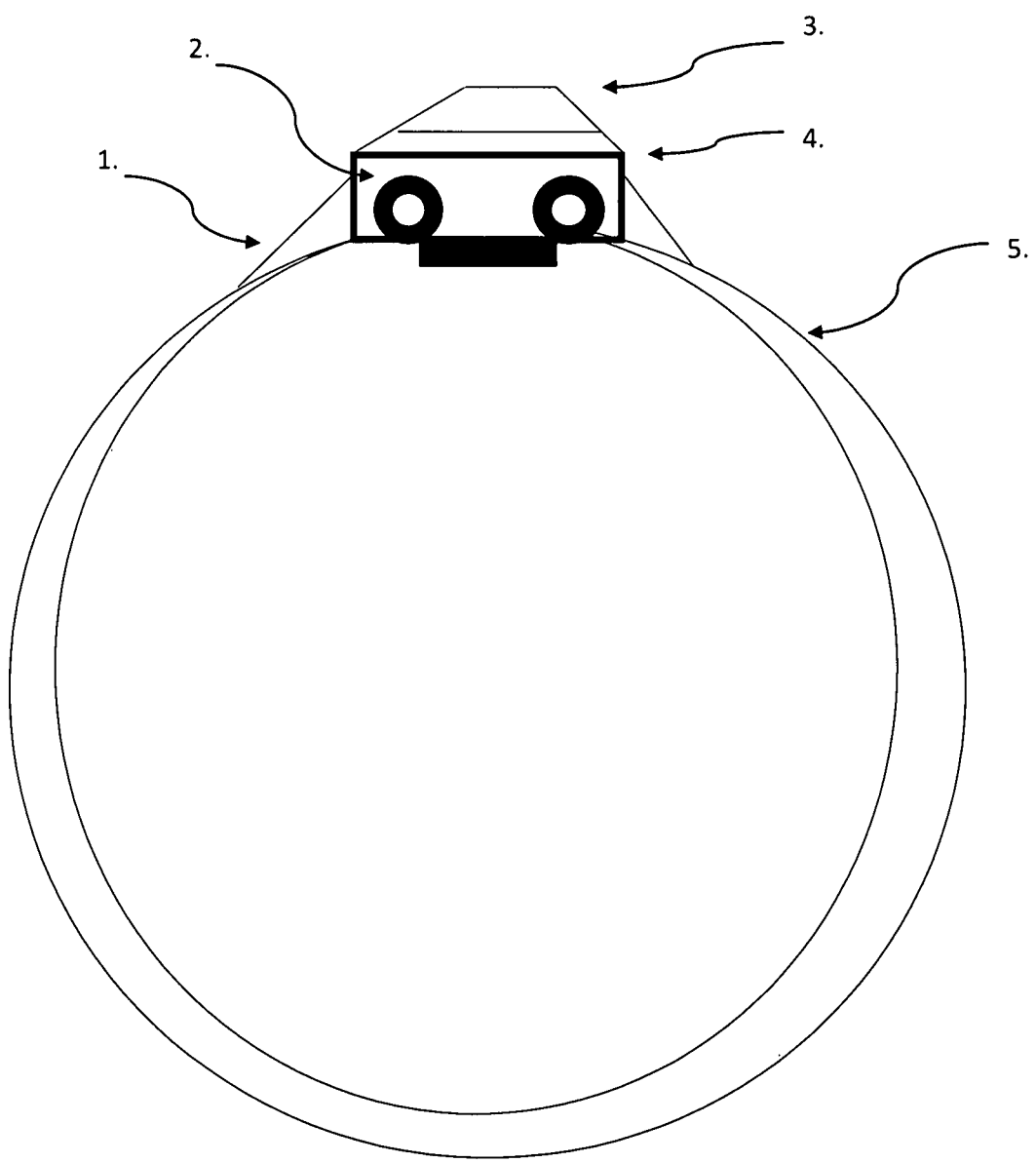
FIGS. 4 and 5 illustrate a wearable arm band having a syringe box that can be pulled into a perpendicular injecting position via a retracting cable.
Figure 5:
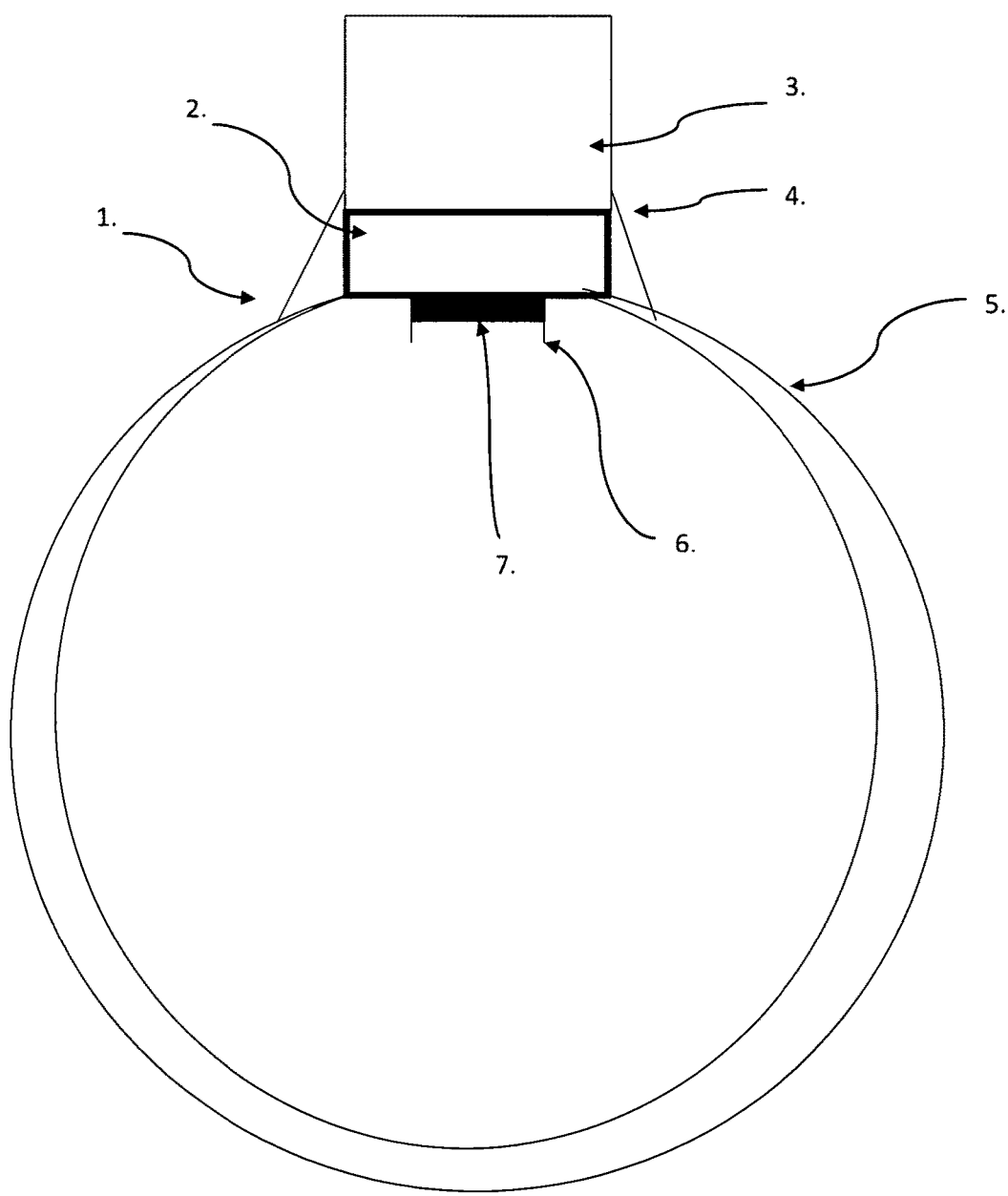

In another preferred embodiment, as illustrated in FIG. 4 and FIG. 5 an armband 5 holds a syringe box 3 which is held flat while not activated, and is pulled into a perpendicular position (FIG. 5) by a tightening retractable cable 1 on the armband 5 and further compressed to inject the antidote(s) into the wearer. The information obtained by the physiological sensor 7 is analyzed by the device computer central processing unit and a diagnosis can be made according to preset algorithms. It then triggers the delivery of the treatment drugs. There may be multiple drugs contained in one delivery system for several different emergency conditions.

This device may be synchronized with an automatic external defibrillator during cardio-pulmonary resuscitation in order to automatically administer medication when needed.

What is claimed is:

1. A wearable medication delivery device comprising:
   a housing;
   a band connected to the housing for attaching the housing to a patient;
   a compressed gas cylinder located inside the housing;
   a piston chamber in fluid communication with the gas cylinder, the fluid path having a gas release valve;
   a piston located in the piston chamber;
   a medication-filled syrette operably connected to the piston;
   a battery to power the device;
   a vital sign sensor; and
   a central processing unit configured to actuate the valve to release the gas, forcing the syrette into the skin, injecting the wearer with the medication, in response to a change in vital signs.

2. The device of claim 1 further comprising a radio-emitter operably connected to the central processing unit wherein activation of the injection is coupled with radio emissions from the device which give real time medical information to incoming emergency medical professionals.

3. A nasal spray device comprising:
   a set of clips configured to spray an antidote into the sinuses;
   a compressed gas cylinder containing the antidote;
   a spray control valve connected between the cylinder and the clips;
   a central processing unit attached to the cylinder having a breathing sensor and a radio emitter; and
   wherein the processing unit is configured to activate the valve to release of the antidote as a nasal mist directly into the sinuses in response to the breathing sensor.

4. A device for spraying an antidote toward a face comprising:
   a face mask comprising a transparent face and upper and lower attachment rods for securing the mask to the head;
   a compressed gas cylinder containing the antidote, the cylinder being attached to the mask;
   a conduit connected between the cylinder and the inside of the mask to release a mist of opiate overdose antidote as a nasal mist into the mask;
   a spray control valve connected between the cylinder and the conduit;
   a central processing unit attached to the mask configured to receive information from sensors capable of detecting an overdose; and
   a radio-emitter connected to the central processing unit, the emitter capable of emitting radio signals with medical information about the wearer when the sensors detect an overdose.

5. The device of claim 1 further comprising:
   a radio-emitter connected to the central processing unit;
   wherein the vital sign sensor is a blood pressure sensor, a pulse rate sensor, or a pulse oximetry sensor; and
   wherein when a predetermined change is detected in the vital sign sensor;
      the valve is actuated; and
      a radio-signal alarm is generated alerting emergency medical technicians.

6. The device of claim 1 wherein the medication is epinephrine.

7. The device of claim 1 wherein the medication is noxalone.

8. The device of claim 1 wherein the medication is a steroid.

9. The device of claim 1 wherein the medication is lidocaine and the vital sign sensor is a heartbeat sensor capable of detecting multiple irregular heartbeats.

10. The device of claim 1 wherein the medication is a blood pressure lowering drug and the vital sign sensor is a blood pressure sensor capable of detecting when the blood pressure is dangerously high.

11. The device of claim 1 wherein the medication is atropine the vital sign sensor is a heartbeat sensor capable of detecting when the pulse is too low.

12. The device of claim 1 further comprising a membrane located between the syrette and a skin surface, the membrane being capable of penetration by the syrette.

13. The device of claim 1 further comprising:
   a radio-emitter operably connected to the central processing unit wherein activation of the injection is coupled with radio emissions from the radio-emitter which give real time medical information to incoming emergency medical professionals;
   a membrane located between the syrette and a skin surface, the membrane being capable of penetration by the syrette; and
   wherein the vital sign sensor is a blood pressure sensor, a pulse rate sensor, or a pulse oximetry sensor.

14. The device of claim 13 wherein the housing is between 1 and 1.5 inches high and has an area of 2 square inches.

* * * * *